(12) United States Patent
Adachi (10) Patent No.: US 11,000,260 B2
(45) Date of Patent: May 11, 2021

(54) ULTRASONIC IMAGING APPARATUS AND METHOD OF CONTROLLING ULTRASONIC IMAGING APPARATUS

(71) Applicant: SOCIONEXT INC., Yokohama (JP)

(72) Inventor: Naoto Adachi, Yokohama (JP)

(73) Assignee: SOCIONEXT INC., Yokohama (JP)

( * ) Notice: Subject to any disclaimer, the term of this patent is extended or adjusted under 35 U.S.C. 154(b) by 669 days.

(21) Appl. No.: 15/725,015

(22) Filed: Oct. 4, 2017

(65) Prior Publication Data

US 2018/0035976 A1 Feb. 8, 2018

Related U.S. Application Data

(63) Continuation of application No. PCT/JP2016/060598, filed on Mar. 31, 2016.

(30) Foreign Application Priority Data

Apr. 17, 2015 (JP) .............................. JP2015-084828

(51) Int. Cl.
*A61B 8/00* (2006.01)
*A61B 8/14* (2006.01)
*A61B 8/08* (2006.01)
*G01S 7/52* (2006.01)
*G10K 11/34* (2006.01)
*G01S 15/89* (2006.01)

(52) U.S. Cl.
CPC .............. *A61B 8/4494* (2013.01); *A61B 8/14* (2013.01); *A61B 8/4488* (2013.01); *A61B 8/48* (2013.01); *A61B 8/5207* (2013.01); *G01S 7/52026* (2013.01); *G01S 15/8915* (2013.01); *G10K 11/346* (2013.01)

(58) Field of Classification Search
None
See application file for complete search history.

(56) References Cited

U.S. PATENT DOCUMENTS

2007/0016048 A1 1/2007 Baba et al.

FOREIGN PATENT DOCUMENTS

JP H08-019537 A 1/1996
JP H08-289891 A 11/1996
(Continued)

OTHER PUBLICATIONS

International Search Report of related International Patent Application No. PCT/JP2016/060598 dated May 24, 2016 (with partial English information).

*Primary Examiner* — Pascal M Bui Pho
*Assistant Examiner* — Marjan Saboktakin
(74) *Attorney, Agent, or Firm* — Arent Fox LLP (57) ABSTRACT

An ultrasonic imaging apparatus includes a plurality of transducers aligned in a line, a select circuit configured to cause transducers selected from the plurality of transducers to transmit an ultrasonic pulse and receive a plurality of received signals, respectively, and a digital signal processing circuit configured to align in time and add up the plurality of received signals weighted by a plurality of respective weighting factors, wherein the digital signal processing circuit changes the plurality of weighting factors according to a time position on the plurality of received signals such that ratios between the plurality of weighting factors change.

4 Claims, 6 Drawing Sheets

(56) References Cited

FOREIGN PATENT DOCUMENTS

| | | | |
|---|---|---|---|
| JP | 2004-283265 | * | 10/2004 |
| JP | 2004-283265 | A | 10/2004 |
| JP | 2007-021192 | A | 2/2007 |
| JP | 2009-005741 | A | 1/2009 |

* cited by examiner

| DEPTH h[mm] | WEIGHTING FACTOR | | | | |
|---|---|---|---|---|---|
| | CHANNEL 1,8 | CHANNEL 2,7 | CHANNEL 3,6 | CHANNEL 4,5 | SUM |
| <10mm | 0 | 0 | (h−10)/40=0 | 1 | 1 |
| 20mm | 0 | (h−20)/40=0 | (h−10)/40=0.25 | 1 | 1.25 |
| 30mm | (h−30)/40=0 | (h−20)/40=0.25 | (h−10)/40=0.5 | 1 | 1.75 |
| 40mm | (h−30)/40=0.25 | (h−20)/40=0.5 | (h−10)/40=0.75 | 1 | 2.5 |
| 50mm | (h−30)/40=0.5 | (h−20)/40=0.75 | (h−10)/40=1 | 1 | 3.25 |
| 60mm | (h−30)/40=0.75 | (h−20)/40=1 | 1 | 1 | 3.75 |
| 70mm< | (h−30)/40=1 | 1 | 1 | 1 | 4 |

FIG.6

ULTRASONIC IMAGING APPARATUS AND METHOD OF CONTROLLING ULTRASONIC IMAGING APPARATUS

CROSS-REFERENCE TO RELATED APPLICATIONS

This application is a continuation application of International Application PCT/JP2016/060598, filed on Mar. 31, 2016 and designated the U.S., which is based upon and claims the benefit of priority from the prior Japanese Patent Application No. 2015-084828 filed on Apr. 17, 2015, with the Japanese Patent Office. The entire contents of these applications are incorporated herein by reference.

BACKGROUND OF THE INVENTION

1. Field of the Invention

The disclosures herein relate to an ultrasonic imaging apparatus and a method of controlling an ultrasonic imaging apparatus.

2. Description of the Related Art

An ultrasonic imaging apparatus such as an ultrasound image diagnosis apparatus has a pulse circuit to apply a pulse voltage signal to a transducer. In response to the pulse voltage signal, the transducer transmits an ultrasonic pulse into a living body. The ultrasonic pulse reflects off the boundary between different living tissues having different acoustic impedances such as a boundary between muscle and fat. The echo is then received by the transducer. A received signal obtained through a single ultrasonic pulse transmission has an amplitude that changes with time. A temporal position in the received signal corresponds to the distance from the transducer to the reflection point in the living body. The amplitude of the received signal corresponds to the magnitude of reflection at the reflection point in the living body. The received signal having the amplitude changing with time that is obtained through a single ultrasonic pulse transmission is displayed on the screen as a bright line having spatial brightness fluctuations that corresponds to a single scan line. A plurality of received signals that are obtained by successively shifting the position of ultrasonic pulse transmission in a horizontal direction are displayed with respective positional shifts on the screen as a plurality of bright lines corresponding to a plurality of scan lines, thereby forming an ultrasound B-mode image.

A transducer array having a large number of transducer elements (i.e., piezoelectric elements) that may be arranged in one dimension, for example, is utilized to scan ultrasonic pulses. Transmission of a single ultrasonic pulse is performed by simultaneously driving m transducer elements among n (m<n) transducer elements arranged in a line. In so doing, pulse voltage signals having slight timing displacements relative to one another may be applied to the m transducer elements to cause the m transducer elements to transmit ultrasonic pulses at slightly different timings. This arrangement allows the transmission aperture having a span corresponding to the m transducer elements to form an ultrasonic beam having a wavefront converging toward a focal point. The position of the m transducer elements driven among the n transducer elements is successively shifted along the one dimensional array, thereby scanning the ultrasonic beam in the lateral direction (i.e., in the direction in which the transducer elements are aligned).

In order to receive echoes, the same m transducer elements that have been used for ultrasonic transmission may be used to receive the echoes. The m transducer elements outputs m received analog signals, respectively, which are then converted into received digital signals by m ADCs (i.e., analog-to-digital converters). The m received digital signals are subjected to delay adjustment such as to eliminate time differences between these signals that are attributable to differences in the distance between the focal point and the m transducer elements. Timing adjustment is thus enabled such that all the received signals have the signal of the echo from the focal point positioned at the same temporal position. All the m received digital signals after the delay adjustment are added up to produce one received digital signal as the result of summation. This one received digital signal is further subjected to noise reduction, gain correction, envelop detection, and the like. The resultant digital signal obtained through these processes may then be displayed on the screen as a single bright line constituting an ultrasound B-mode image.

Recently, there has been an expectation for a mobile version of an ultrasonic imaging apparatus, which has prompted efforts to reduce the size and power consumption of apparatus. The purpose of reducing the size and power consumption of apparatus may be attained by reducing the number of ADCs or by lowering the drive voltage of transducers. In a typical expensive ultrasound image diagnosis apparatus for medical use, the number of ADC channels, i.e., the number of transducer elements simultaneously driven for transmission and reception, may be 32 or 64, for example, which provides an ultrasonic beam having a high focusing ability that provides a high-quality image. The number of ADC channels, i.e., the number of simultaneously driven transducer elements, may be reduced for the purposes of size reduction and lower power consumption. Such a modification, however, may give rise to the problem of degraded image quality because the modification weakens the combined intensity of ultrasonic pulses and received signals and also lowers the focusing ability. Accordingly, there may be a need to reduce image degradation while reducing the number of channels to effectively lower power consumption.

Recently, there has been an expectation for a mobile version of an ultrasonic imaging apparatus, which has prompted efforts to reduce the size and power consumption of apparatus. The purpose of reducing the size and power consumption of apparatus may be attained by reducing the number of ADCs or by lowering the drive voltage of transducers. In a typical expensive ultrasound image diagnosis apparatus for medical use, the number of ADC channels, i.e., the number of transducer elements simultaneously driven for transmission and reception, may be 32 or 64, for example, which provides an ultrasonic beam having a high focusing ability that provides a high-quality image. Reducing the number of ADC channels, i.e., the number of simultaneously driven transducer elements, for the purposes of size reduction and lower power consumption may degrade image quality because of the weakened combined intensity of ultrasonic pulses and received signals.

Accordingly, it may be desirable to reduce image quality degradation while reducing the number of channels in an ultrasonic imaging apparatus.

RELATED-ART DOCUMENTS

Patent Document

[Patent Document 1] Japanese Laid-open Patent Publication No. 2007-21192

[Patent Document 2] Japanese Laid-open Patent Publication No. 2009-5741

SUMMARY OF THE INVENTION

It is a general object of the present invention to provide an ultrasonic imaging apparatus that substantially obviates one or more problems caused by the limitations and disadvantages of the related art.

An ultrasonic imaging apparatus includes a plurality of transducers aligned in a line, a select circuit configured to cause transducers selected from the plurality of transducers to transmit an ultrasonic pulse and receive a plurality of received signals, respectively, and a digital signal processing circuit configured to align in time and add up the plurality of received signals weighted by a plurality of respective weighting factors, wherein the digital signal processing circuit changes the plurality of weighting factors according to a time position on the plurality of received signals such that ratios between the plurality of weighting factors change.

DESCRIPTION OF THE PREFERRED EMBODIMENTS

In the following, embodiments of the present invention will be described with reference to the accompanying drawings.

In the following, embodiments of the invention will be described with reference to the accompanying drawings. In these drawings, the same or corresponding elements are referred to by the same or corresponding numerals, and a description thereof will be omitted as appropriate.

Figure 1:
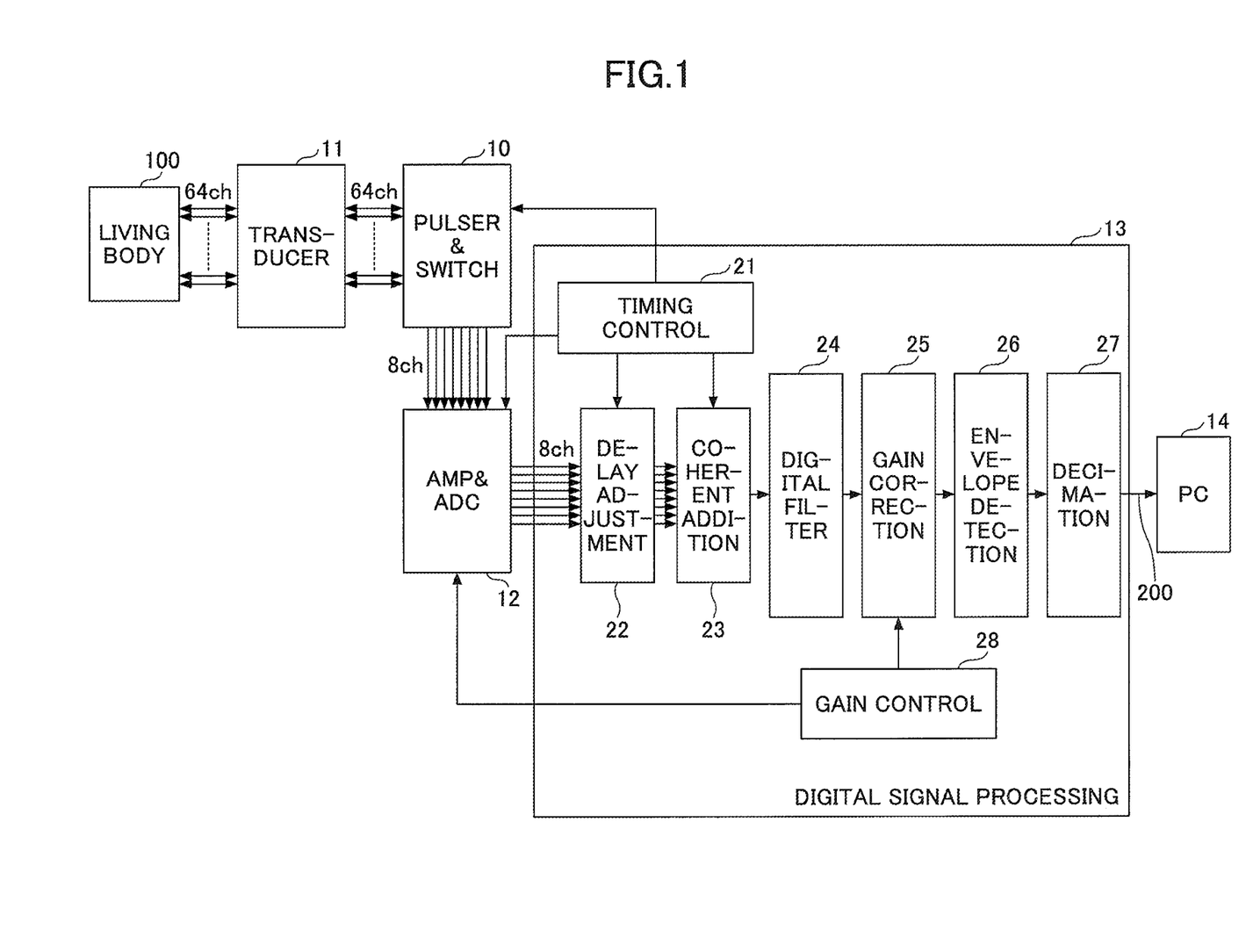
FIG. 1 is a drawing illustrating an example of the configuration of an ultrasonic imaging apparatus.

FIG. 1 is a drawing illustrating an example of the configuration of an ultrasonic imaging apparatus. The ultrasonic imaging apparatus illustrated in FIG. 1 includes a pulser-and-switch circuit 10, a transducer array 11, an amplifier-and-AD-converter circuit (AMP&ADC) 12, and a digital signal processing circuit 13. The digital signal processing circuit 13 includes a timing control circuit 21, a delay adjustment circuit 22, a coherent addition circuit 23, a digital filter 24, a gain correction circuit 25, an envelope detecting circuit 26, a decimating circuit 27, and a gain control circuit 28. Data of ultrasound B-mode image of a living body 100 generated by the ultrasonic imaging apparatus may be transmitted to an information processing and display apparatus such as a personal computer (PC) 14 or a tablet through an interface 200 such as Bluetooth.

In FIG. 1 and the subsequent similar drawings, boundaries between functional or circuit blocks illustrated as boxes basically indicate functional boundaries, and may not correspond to separation in terms of physical positions, separation in terms of electrical signals, separation in terms of control logic, etc. Each functional or circuit block may be a hardware module that is physically separated from other blocks to some extent, or may indicate a function in a hardware module in which this and other blocks are physically combined together.

The transducer array 11 has a plurality (64 in the example illustrated in FIG. 1) of transducer elements arranged in a line. The pulser-and-switch circuit 10 causes a plurality (i.e., 8 in the example illustrated in FIG. 1) of transducer elements selected from the plurality of transducer elements of the transducer array 11 arranged in a line to transmit an ultrasonic pulse and receive echo signals, respectively. Specifically, under the control of the timing control circuit 21 of the digital signal processing circuit 13, the pulser-and-switch circuit 10 applies pulse voltage signals to the plurality of selected transducer elements consecutively arranged in the alignment direction of the transducer array 11. In response to the pulse voltage signals, the plurality of transducer elements transmits an ultrasonic pulse into the living body 100. The ultrasonic pulse reflects off the boundary between different living tissues having different acoustic impedances such as a boundary between muscle and fat. The echo is then received by the above-noted selected transducer elements.

In the case of 8 transducer elements being driven together, pulse voltage signals having slight timing displacements relative to one another are applied to these 8 transducer elements, thereby causing the 8 transducer elements to transmit ultrasonic pulses at respective, slightly different timings. This arrangement allows the transmission aperture having a span corresponding to the 8 transducer elements to form an ultrasonic beam having a wavefront converging toward a focal point. The position of the 8 transducer elements driven among the 64 transducer elements of the transducer array 11 is successively shifted along the one dimensional array, thereby scanning the ultrasonic beam in the lateral direction (i.e., in the direction in which the transducer elements are aligned). The timing at which the pulse voltage signals are applied to the 8 transducer elements may be controlled by the timing control circuit 21 of the digital signal processing circuit 13.

In order to receive echoes, the same 8 transducer elements that have been used for ultrasonic transmission may be used to receive the echoes. 8 received analog signals output from the 8 transducer elements are supplied to and amplified by the amplifier-and-AD-converter circuit 12, followed by being converted into received digital signals by the 8 ADCs (i.e., analog-to-digital converters) of the amplifier-and-AD-converter circuit 12. The amplifier-and-AD-converter circuit 12 then supplies the converted received digital signals to the delay adjustment circuit 22 of the digital signal processing circuit 13.

The 8 received digital signals are subjected to delay adjustment by the delay adjustment circuit 22 such as to eliminate time differences between these signals that are attributable to differences in the distance between the focal point and the 8 transducer elements. Timing adjustment is thus enabled such that all the received signals have the signal of the echo from the focal point positioned at the same temporal position. The 8 received digital signals having delays adjusted to be aligned in time are weighted with respective weighting factors and then added up by the coherent addition circuit 23, which thus produces one received digital signal as the result of summation. This one received digital signal is then subjected to noise removal by the digital filter 24, gain correction by the gain correction circuit 25, envelop detection by the envelope detecting circuit 26, and the like. The decimating circuit 27 selects subsample scan lines or subsample pixels according to need, thereby to generate image data suitable for the format of image display. The weighting process performed by the coherent addition circuit 23 will be described later in detail.

The gain correction circuit 25 operates under the control of the gain control circuit 28 so as to amplify the amplitude of a received digital signal such that the later the position of a point of interest in the received signal is, the greater the corresponding amplification factor is. Namely, as the distance from the transducer array 11 to a point of reflection in the living body 100 increases, the amplification factor to amplify the amplitude of a signal received from that point increases.

In the ultrasonic imaging apparatus illustrated in FIG. 1, 8 transducer elements are selectively driven under the control of the digital signal processing circuit 13. In the transmission operation, pulse voltage signals applied to the transducer elements have delays that are symmetrical between two sides across the center which is a point between the two central transducer elements in the direction in which the transducer elements of the transducer array 11 are aligned. In the signal processing after reception, the 8 received signals arranged in an order corresponding to the aligned array of the transducer elements of the transducer array 11 are added up after being given respective delays that are symmetrical between two sides across the center which is situated between the two central signals.

Figure 2:
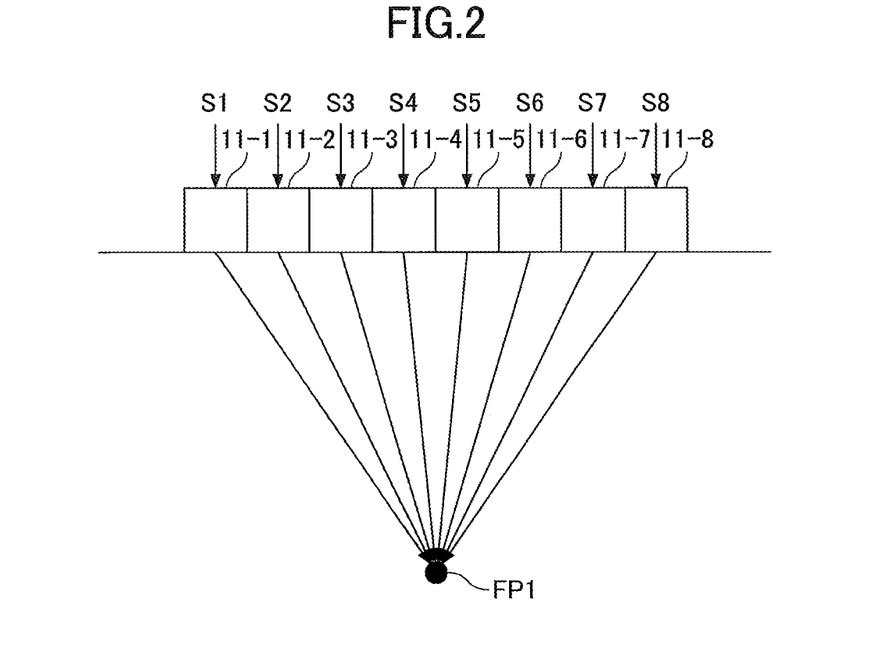
FIG. 2 is a drawing illustrating an example of a transmission operation for which 8 transducer elements are selectively driven.

FIG. 2 is a drawing illustrating an example of a transmission operation for which 8 transducer elements are selectively driven. In FIG. 2, transducer elements 11-1 through 11-8 are 8 consecutive transducer elements among a plurality (e.g., 64) of transducer elements of the transducer array 11 arranged in a line. As pulse voltage signals S1 through S8 are applied to the 8 transducer elements 11-1 through 11-8, respectively, the transducer elements 11-1 through 11-8 transmit an ultrasonic pulse toward a focal point FP1. In so doing, the pulse voltage signals S1 and S8 are first applied to the transducer elements 11-1 and 11-8 situated at the opposite ends, respectively. Upon the passage of a predetermined delay time thereafter, the pulse voltage signals S2 and S7 are applied to the transducer elements 11-2 and 11-7, respectively, which are the second ones from the opposite ends. Upon the passage of a predetermined delay time thereafter, the pulse voltage signals S3 and S6 are applied to the transducer elements 11-3 and 11-6, respectively, which are the third ones from the opposite ends. Upon the passage of a predetermined delay time thereafter, the pulse voltage signals S4 and S5 are applied to the transducer elements 11-4 and 11-5, respectively, which are the fourth ones from the opposite ends. Namely, the transducer elements 11-1 through 11-8 of the transducer array 11 transmit an ultrasonic pulse with respective delays that are symmetrical between two sides across the center which is a point between the two central transducer elements, such that the closer to the center the transducer element is, the greater the delay is. This arrangement allows the transducer elements 11-1 through 11-8 to transmit an ultrasonic pulse having a wavefront converging toward the focal point FS1.

Figure 3:
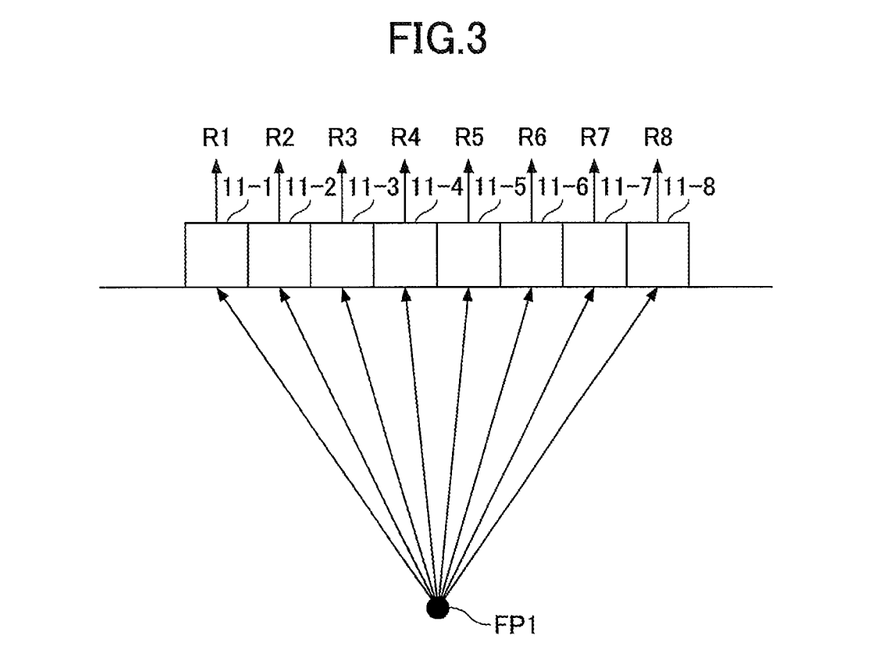
FIG. 3 is a drawing illustrating an example of a reception operation for which 8 transducer elements are selectively driven.

FIG. 3 is a drawing illustrating an example of a reception operation for which 8 transducer elements are selectively driven. In FIG. 3, the transducer elements 11-1 through 11-8, which are 8 consecutive transducer elements among a plurality (e.g., 64) of transducer elements of the transducer array 11 arranged in a line, receive echoes from the focal point FP1. Received signals R1 through R8 detected by the transducer elements 11-1 through 11-8 are supplied to the delay adjustment circuit 22 through the pulser-and-switch circuit 10 and the amplifier-and-AD-converter circuit 12, and are then given respective delays by the delay adjustment circuit 22. In so doing, no delay, for example, may be imposed on the received signals R1 and R8 corresponding to the transducer elements 11-1 and 11-8 situated at the opposite ends. A predetermined first delay is imposed on the received signals R2 and R7 corresponding to the two transducer elements 11-2 and 11-7 that are the second ones from the opposite ends. Further, a second delay which is longer than the first delay is imposed on the received signals R3 and R6 corresponding to the two transducer elements 11-3 and 11-6 that are the third ones from the opposite ends. A third delay which is longer than the second delay is imposed on the received signals R4 and R5 corresponding to the two transducer elements 11-4 and 11-5 that are the fourth ones from the opposite ends. Namely, the 8 received signals corresponding to the transducer elements 11-1 through 11-8 of the transducer array 11 are given respective delays that are symmetrical between two sides across the center which is a point between the two central transducer elements, such that the closer to the center the transducer element is, the greater the delay is. With this arrangement, the received signals corresponding to the ultrasonic pulse from the focal point FS1 received by the transducer elements 11-1 through 11-8 are aligned at the same position on the time axis for provision to the coherent addition process.

Figure 4:
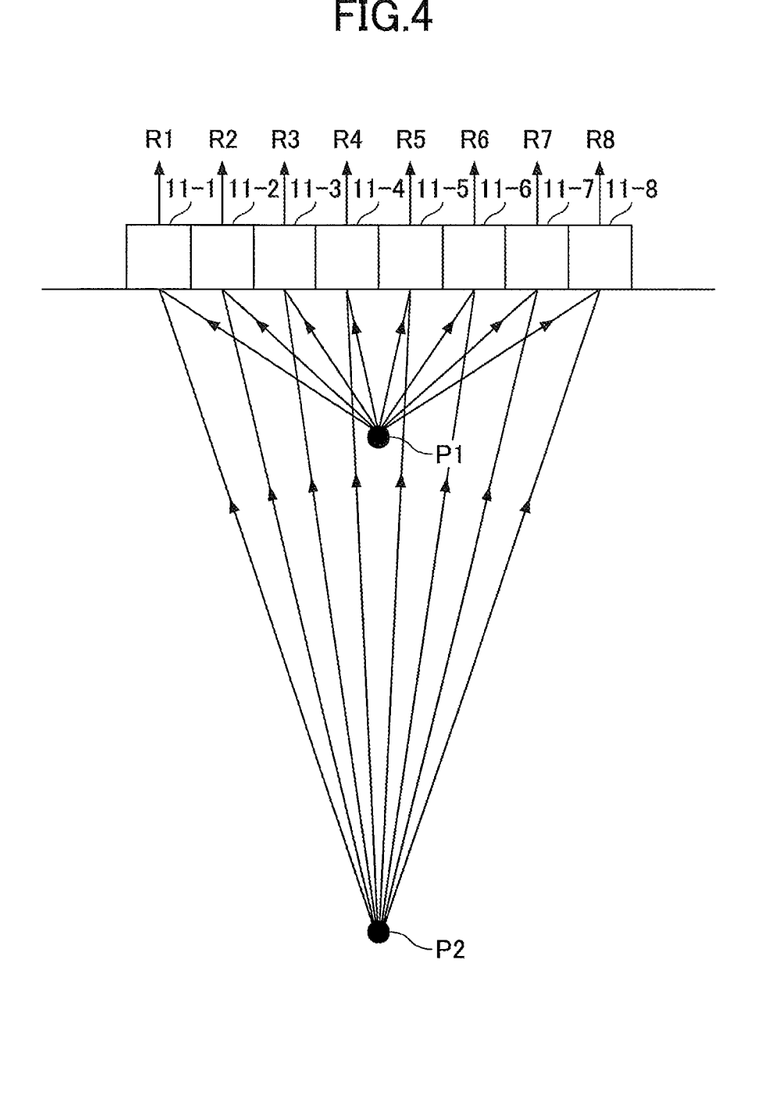
FIG. 4 is a drawing illustrating an example of the operation of 8 transducer elements receiving echoes from different positions in a depth direction.

FIG. 4 is a drawing illustrating an example of the operation of 8 transducer elements receiving echoes from different positions in the depth direction. In FIG. 4, the 8 transducer elements 11-1 through 11-8 receive echoes from a point P1 and echoes from a point P2, thereby producing 8 received signals R1 through R8, respectively. It may be noted that at the time of preceding transmission, the 8 transducer elements 11-1 through 11-8 received pulse voltage signals, respectively, in the same or similar manner as illustrated in FIG. 2, and transmitted an ultrasonic pulse converging onto a desired focal point.

The position of the focal point does not matter for the illustration of the case in FIG. 4. For the sake of convenience, however, the focal point is set at a midpoint between the point P1 and the point P2. In this case, echoes not only arrive at the transducer elements 11-1 through 11-8 from the focal point, but also arrive at the transducer elements 11-1 through 11-8 from the point P1 closer than the focal point and from the point P2 farther away than the focal point through the paths as illustrated in FIG. 4. Echoes from different positions in the depth direction arrive at the transducer elements 11-1 through 11-8 at respective, different points in time, and thus appear as amplitude features in the received signals at different positions on the time axis.

In the ultrasonic imaging apparatus illustrated in FIG. 1, the delay adjustment circuit 22 of the digital signal processing circuit 13 adjusts the relative timing of the 8 received signals R1 through R8 such that the focal point situated at the midpoint between the point P1 and the point P2 is placed at the same position on the time axis. Further, the coherent addition circuit 23 adds up the 8 received signals after the timing adjustment. In doing so, the received signals R1 through R8 from the point P2 at a further distance have a reduced echo amplitude due to the attenuation of ultrasonic waves inside a living body, so that it is preferable to use as many received signals as possible for coherent addition. It should be noted, however, that the time difference between the signals of ultrasonic pulse echoes from the focal point in the received signals R1 through R8 are different from the time difference between the signals of ultrasonic pulse echoes from the point P2 in the received signals R1 through R8. The delay adjustment circuit 22 adjusts the relative timing of the received signals R1 through R8 such that the position of the echo pulse from the focal point is aligned at the same position on the time axis, so that coherent addition by the coherent addition circuit 23 adds up the echoes from the point P2 with slight positional displacements. Since the distances between the point P2 and the transducer elements 11-1 through 11-8 are relatively long, however, the temporal positions of the echoes from the point P2 in the 8 received signals R1 through R8 are not so different from each other. Coherent addition of the 8 received signals R1 through R8 thus results in the echo from the point P2 being relatively clear in the added received signal.

The received signals R1 through R8 from the point P1 at a shorter distance have a sufficiently strong echo amplitude because the ultrasound waves experience only a small attenuation inside the living body, so that it suffices to use a small number of received signals for coherent addition. The delay adjustment circuit 22 adjusts the relative timing of the received signals R1 through R8 such that the position of the ultrasonic echo pulse from the focal point is aligned at the same position on the time axis, so that coherent addition by the coherent addition circuit 23 adds up the echoes from the point P1 with positional displacements. Since the distances between the point P1 and the transducer elements 11-1 through 11-8 are relatively short in this case, the temporal positions of the echoes from the point P1 in the 8 received signals R1 through R8 are significantly different from each other. Coherent addition of the 8 received signals R1 through R8 thus results in the echo from the point P1 being an unclear, blurred signal waveform in the added received signal. It may be even preferable to reduce the number of received signals used for coherent addition, e.g., to use only the received signals of the transducer elements 11-4 and 11-5 for coherent addition, so that a clear echo image of the point P1 may possibly appear.

In consideration of the above, the coherent addition circuit 23 of the digital signal processing circuit 13 in the ultrasonic imaging apparatus illustrated in FIG. 1 performs coherent addition of the received signals that are given different weighting factors responsive to the temporal positions of the received signals, i.e., responsive to the position in the depth direction in a living body. Namely, the coherent addition circuit 23 operates under the control of the timing control circuit 21 to change the weighting factors in response to the temporal positions of the received signals, such that the ratios between the weighting factors change, i.e., the differences between the weighting factors change. An example will be described in which a first received signal among a plurality of received signals is given a first weighting factor among a plurality of weighting factors, and a second received signal among the plurality of received signals is given a second weighting factor among the plurality of weighting factors. In the array of received signals arranged in an order corresponding to the aligned array of the transducer elements, the first received signal is situated closer to the center than the second received signal is. In this case, the first weighting factor has a greater value than the second weighting factor. In more general terms, the closer the received signal is to the center in the array of received signals, the greater the assigned weighting factor is, and the closer to the ends the received signal is, the smaller the assigned weighting factor is.

The digital signal processing circuit 13 increases the ratio between the first weighting factor and the second weighting factor as the point of interest moves earlier in time in the received signal. In more general terms, the digital signal processing circuit 13 sets the ratio (or difference) between the greater weighting factor assigned to the received signal close to the center in the array of received signals and the smaller weighting factor assigned to the received signal close to either end, such that the ratio increases toward an earlier time position. Namely, as the distance from the transducer array 11 to a point of reflection in the living body 100 decreases, the amplification factor to amplify the amplitude of a signal received from that point decreases with a greater amount for the received signal close to the end. In this case, the weighting factor for the received signal close to the end may be set to zero, thereby making the signal amplitude zero.

Figure 5:
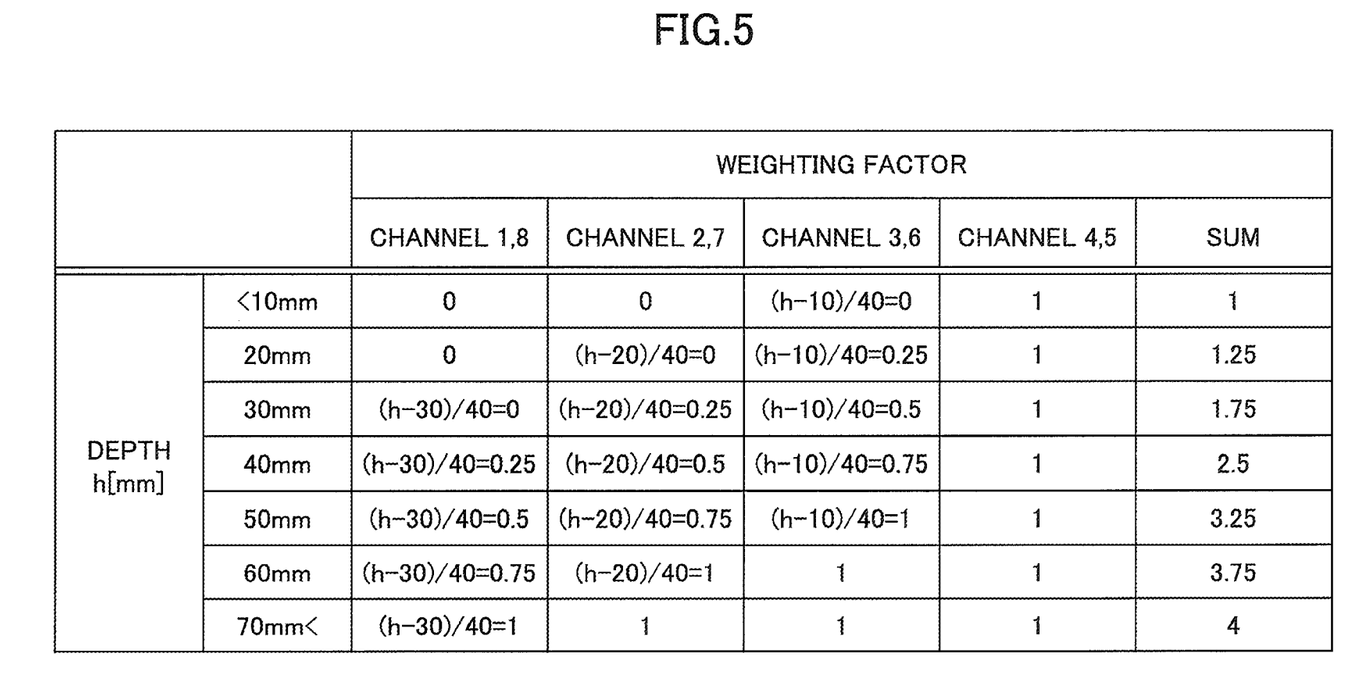
FIG. 5 is a drawing illustrating an example of weighting factors.

FIG. 5 is a drawing illustrating an example of weighting factors. Based on the weighting factors illustrated in FIG. 5, the coherent addition circuit 23 illustrated in FIG. 1 may assign weighting factors to the received signals. The weighting factors illustrated in FIG. 5 are represented as formulas for changing the weighting factors of respective channels linearly in response to the position in the depth direction. 8 received signals arranged in one-to-one correspondence with 8 transducer elements arranged according to the alignment of transducer elements of the transducer array 11 are denoted as a channel 1 through a channel 8 sequentially from one end thereof. The channel 1 and the channel 8 (i.e., the received signals at the opposite ends) are given weighting factors whose values are $(h-30)/40$ at a depth h (mm). In the case of h being smaller than or equal to 30 mm, however, the value of the weighting factor is set to zero. In the case of h being greater than or equal to 70 mm, the value of the weighting factor is set to "1". The channel 2 and the channel 7 (i.e., the received signals second from the opposite ends) are given weighting factors whose values are $(h-20)/40$ at a depth h (mm). In the case of h being smaller than or equal to 20 mm, however, the value of the weighting factor is set to zero. In the case of h being greater than or equal to 60 mm, the value of the weighting factor is set to "1". The channel 3 and the channel 6 (i.e., the received signals third from the opposite ends) are given weighting factors whose values are $(h-10)/40$ at a depth h (mm). In the case of h being smaller than or equal to 10 mm, however, the value of the weighting factor is set to zero. In the case of h being greater than or equal to 50 mm, the value of the weighting factor is set to "1". The channel 4 and the channel 5 (i.e., the two received signals at the center) are given weighting factors whose value is "1" regardless of the depth.

The table of weighting factors illustrated in FIG. 5 provides the value of a weighting factor of each channel at the point at which the depth h is 10 mm, 20 mm, 30 mm, 40 mm, 50 mm, 60 mm, or 70 mm. The leftmost column provides the sum of weighting factors. Since two channels having the same weighting factor are illustrated at the same column, only four weighting factors are provided in FIG. 5, and the value of the sum is the sum of these four weighting factors. Accordingly, the sum of 8 weighting factors of the 8 channels is twice the value of the sum illustrated in FIG. 5. Upon coherent addition by the coherent addition circuit 23, the result of coherent addition is divided by the sum of weighting factors in order to normalize each result of addition.

As can be seen from the values of factors illustrated in FIG. 5, the values of weighting factors by which respective received signals are multiplied have such values as to enhance channels at the center of the 8 channels at a position corresponding to a small depth h, i.e., an early time position in the received signals. As the value of the depth h increases, i.e., as the time point of interest in the received signals moves to a later position, the values of weighting factors used to multiply the respective received signals change such that not only the center portion of the 8 channels but also channels closer to the ends are used. When the value of the depth h sufficiently increases, i.e., when the time point of interest in the received signals moves to a sufficiently late point, the values of weighting factors used to multiply the respective received signals become the same for the 8 channels.

FIG. 5 provides formulas for the weighting factors that linearly change in response to the depth h. Alternatively, only the weighting factors as observed at the points at which the depth h is 10 mm, 20 mm, 30 mm, 40 mm, 50 mm, 60 mm, and 70 mm, respectively, may be used, such that the weighting factors exhibit step-like changes according to the depth. Namely, the weighting factors at a depth of 10 mm are used for the depth range from 10 mm to 20 mm, and the weighting factors at a depth of 20 mm are used for the depth range from 20 mm to 30 mm, with the weighting factors at a depth of 30 mm being used for the depth range from 30 mm to 40 mm, for example. Further, for the depth range beyond 70 mm, the weighting factors at a depth of 70 mm may be used. The table of weighting factors defined at the points at which the depth h is 10 mm, 20 mm, 30 mm, 40 mm, 50 mm, 60 mm, and 70 mm, respectively, as illustrated in FIG. 5 may be prepared and referred to in response to depth information, so as to obtain weighting factors used to multiply the received signals in response to the depth. Alternatively, the hardware for calculating the formulas illustrated in FIG. 5 may be provided to calculate the formulas by using the value of the variable h indicative of a depth as the input thereinto, thereby obtaining weighting factors used to multiply the received signals in response to the depth.

Figure 6:
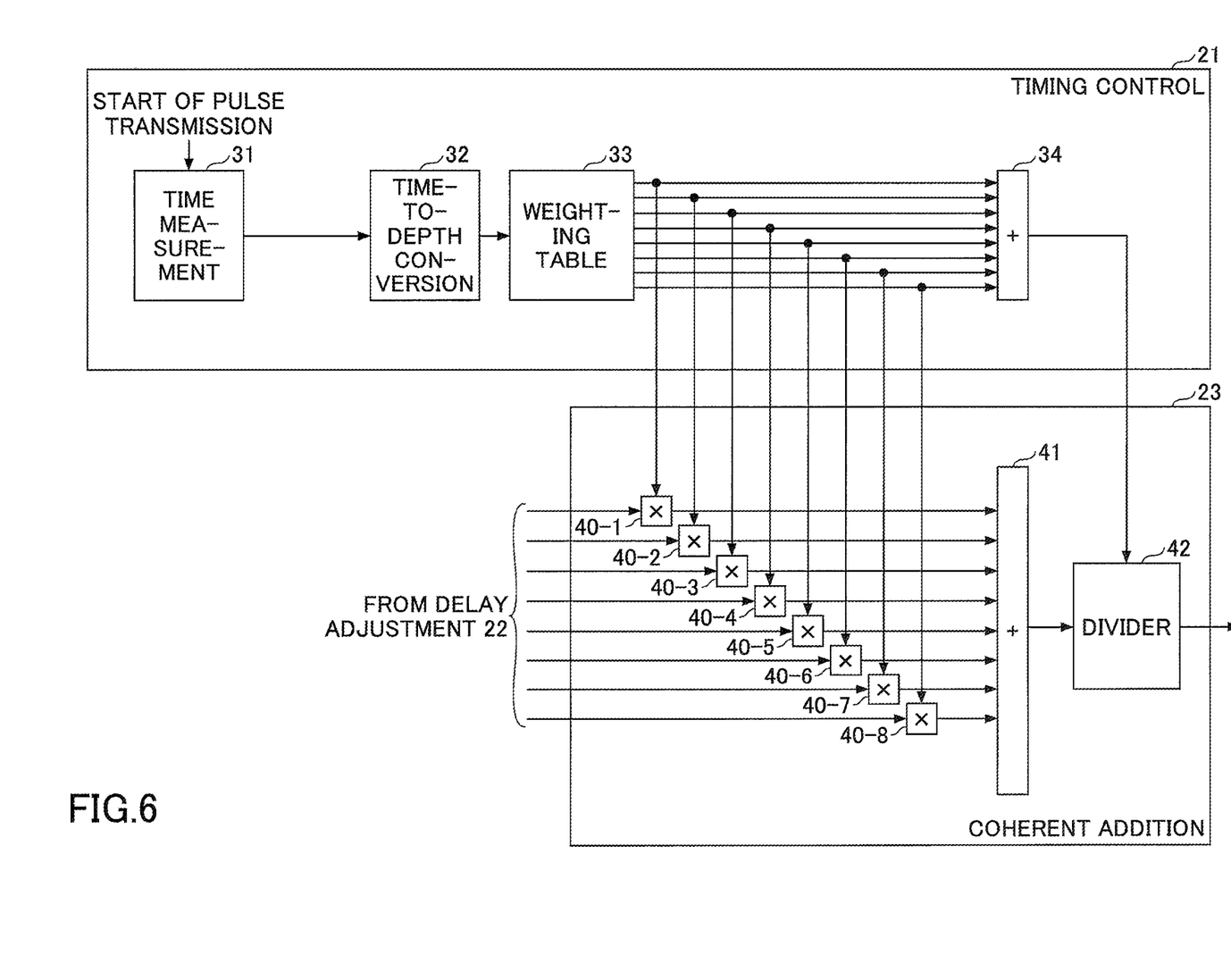
FIG. 6 is a drawing illustrating an example of the configuration of a timing control circuit and a coherent addition circuit.

FIG. 6 is a drawing illustrating an example of the configuration of the timing control circuit 21 and the coherent addition circuit 23. In FIG. 6, the timing control circuit 21 includes a time measurement circuit 31, a time-to-depth conversion circuit 32, a weighting table 33, and an adder 34. The coherent addition circuit 23 includes multipliers 40-1 through 40-8, an adder 41, and a divider 42.

The time measurement circuit 31 receives a signal indicative of the start of pulse transmission at the time the transducer array 11 starts pulse transmission. As previously described, under the control of the timing control circuit 21 of the digital signal processing circuit 13, the pulser-and-switch circuit 10 applies pulse voltage signals to the plurality of selected transducer elements of the transducer array 11. In synchronization with the timing at which the timing control circuit 21 instructs the pulser-and-switch circuit 10 to apply pulse voltage signals, the above-noted signal indicative of the start of pulse transmission may be applied to the time measurement circuit 31. Immediately after the transducer array 11 transmits an ultrasonic pulse, the transducer array 11 starts to receive echoes and starts to output received signals. A length of time passage measured by the time measurement circuit 31 from the start of pulse transmission is used to determine a length of time passage from the start of echo reception in the received signal output from the transducer array 11. The time measurement circuit 31 consecutively produces data indicative of the length of time passage that increases with time.

The time-to-depth conversion circuit 32 converts the length of time passage measured by the transducer array 11 into depth information. Namely, the length of time passage is multiplied by the speed of sound, and, then, the result of multiplication is halved to calculate the distance in the depth direction. This distance indicates the distance in the depth direction to the reflection point that has reflected the signal component situated at the time position corresponding to the length of time passage.

The weighting table 33 may have the weighting factors at the points at which the depth h is 10 mm, 20 mm, 30 mm, 40 mm, 50 mm, 60 mm, and 70 mm, respectively, as illustrated in FIG. 5 previously described. The weighting table 33 is referred to in response to the depth information supplied from the time-to-depth conversion circuit 32, thereby outputting 8 weighting factors responsive to the depth for the 8 channels.

The adder 34 calculates the sum of the 8 weighting factors output from the weighting table 33. The 8 weighting factors output from the weighting table 33 and the sum produced by the adder 34 are supplied to the coherent addition circuit 23. Alternatively, the values of sums may be provided as entries in the weighting table 33, so that the value of the sum responsive to the depth information input into the weighting table 33 may be output from the weighting table 33 together with the 8 weighting factors. The 8 weighting factors and the sum supplied from the timing control circuit 21 to the coherent addition circuit 23 have values that successively change with time.

The multipliers 40-1 through 40-8 of the coherent addition circuit 23 multiply the 8 received signals from the delay adjustment circuit 22 by the 8 weighting factors supplied from the timing control circuit 21, respectively, thereby producing 8 weighted received signals. The adder 41 adds up the 8 weighted received signals to output a single received signal as the result of addition. The received signal obtained by the adder 41 as the result of addition is divided by the sum of the weighting factors by the divider 42, so that the received signal after the coherent addition by the coherent addition circuit 23 is normalized into a signal having a proper amplitude irrespective of the position on the time axis.

Figure 7:
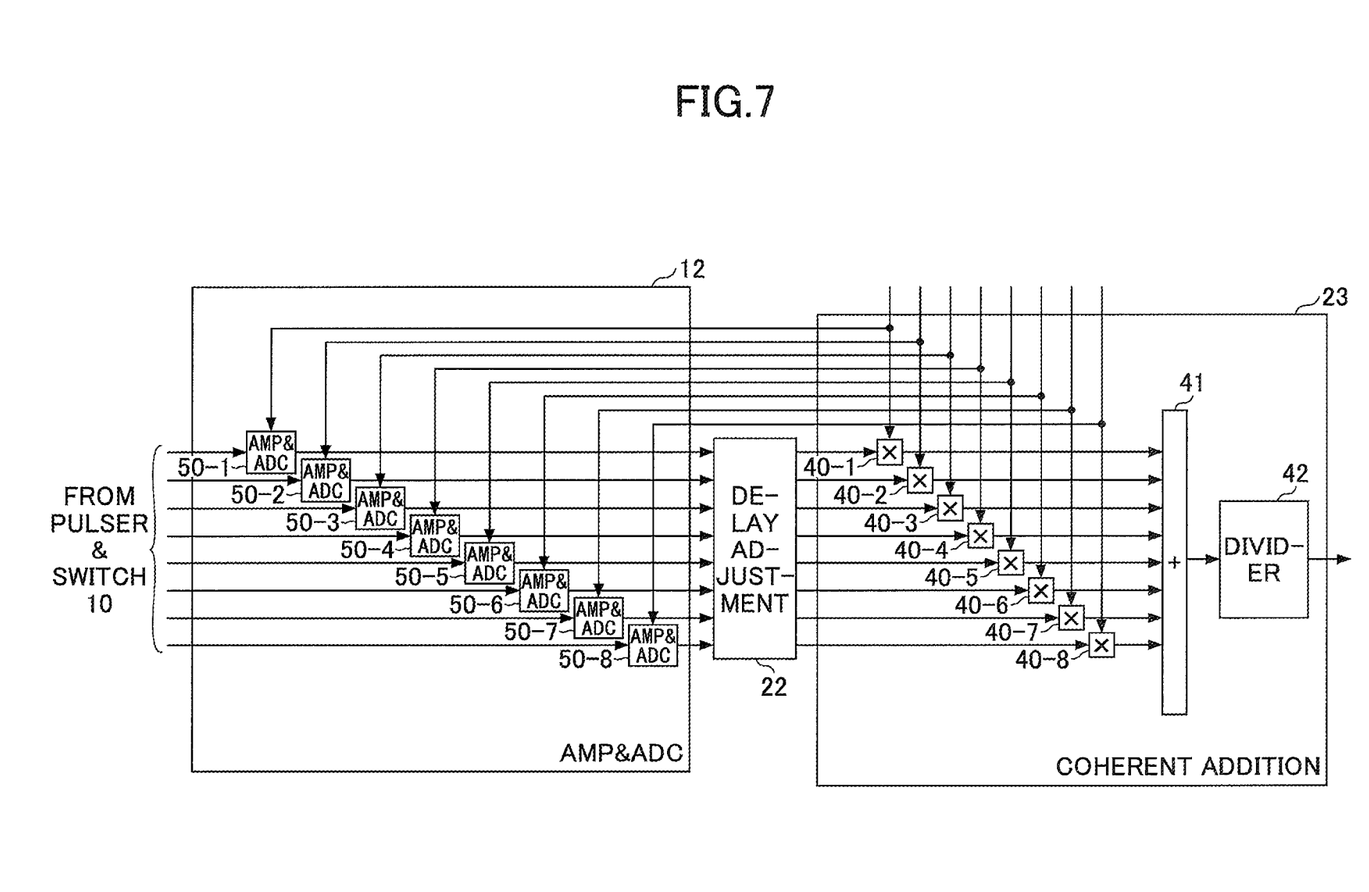
FIG. 7 is a drawing illustrating an example of the configuration of an amplifier-and-AD-converter circuit.

FIG. 7 is a drawing illustrating an example of the configuration of the amplifier-and-AD-converter circuit 12. The amplifier-and-AD-converter circuit 12 illustrated in FIG. 7 includes a plurality of AMP&ADCs 50-1 through 50-8 having an amplification function and an AD conversion function.

The AMP&ADCs 50-1 through 50-8 receive the received signals from the pulser-and-switch circuit 10, and amplify these received signals. The AMP&ADCs 50-1 through 50-8 further convert the amplified received signals from analog signals into digital signals, followed by supplying the converted received signals to the delay adjustment circuit 22 of the digital signal processing circuit 13. As illustrated in FIG. 6, the 8 weighting factors supplied from the timing control circuit 21 to the coherent addition circuit 23 are supplied to the AMP&ADCs 50-1 through 50-8, respectively. In the case of the supplied weighting factors being zero, the AMP&ADCs 50-1 through 50-8 stop amplifying and AD-converting. For example, circuits may be provided that output HIGH in the case of zero weighting factors and that output LOW in the case of non-zero weighting factors. The outputs of such circuits may be applied to switch circuits such as PMOS transistors to control the opening and closing of the switches. A power supply voltage may be supplied to the AMP&ADCs 50-1 through 50-8 through these switches, which enables the occurrence of zero weighting factors to block the power supply of the corresponding AMP&ADSs and to stop the operations thereof. This arrangement serves to stop the operations of unneeded ones of the AMP&ADCs 50-1 through 50-8, thereby reducing power consumption accordingly.

According to at least one embodiment, an ultrasonic imaging apparatus is able to reduce image quality degradation while reducing the number of channels.

Further, although the present invention has been described with reference to the embodiments, the present invention is not limited to these embodiments, and various variations and modifications may be made without departing from the scope as defined in the claims.

What is claimed is:

1. An ultrasonic imaging apparatus, comprising:
   a plurality of transducers aligned in a line;
   a select circuit configured to select and cause transducers selected from the plurality of transducers to transmit an ultrasonic pulse and receive a plurality of received signals, respectively;
   a digital signal processing circuit configured to add up the plurality of received signals weighted by a plurality of respective weighting factors, and
   a plurality of analog to digital (AD) converters configured to convert the plurality of received signals from analog signals into digital signals and to supply the converted received signals to the digital signal processing circuit,
   wherein the digital signal processing circuit changes the plurality of weighting factors such that ratios between the plurality of weighting factors change,
   wherein the plurality of received signals includes a first received signal and a second received signal, and each of the received signals has a first signal portion corresponding to a first depth and a second signal portion corresponding to a second depth, the first signal portion of each of the received signals being reflected from a portion of an object situated at the first depth into the object, the second signal portion of each of the received signals being reflected from a portion of the object situated at the second depth into the object, the first received signal being weighted by a first weighting factor, the second received signal being weighted by a second weighting factor, a ratio of the first weighting factor to the second weighting factor for the first signal portion being different from a ratio of the first weighting factor to the second weighting factor for the second signal portion, and
   wherein upon an occurrence that the digital signal processing circuit sets at least one of the plurality of weighting factors to zero, power is stopped from being supplied to at least one of the plurality of AD converters, which corresponds to a received signal assigned to the at least one weighting factor set to zero.

2. The ultrasonic imaging apparatus as claimed in claim 1, wherein the first received signal is situated closer to a center than the second received signal in an aligned array of the received signals arranged in an order corresponding to an aligned array of the plurality of transducers.

3. The ultrasonic imaging apparatus as claimed in claim 2, wherein the ratio of the first weighting factor to the second weighting factor for the first signal portion is greater than the ratio of the first weighting factor to the second weighting factor for the second signal portion.

4. A method of controlling an ultrasonic imaging apparatus, comprising:
   selecting and causing transducers selected from a plurality of transducers aligned in a line to transmit an ultrasonic pulse and receive a plurality of received signals, respectively;
   adding up the plurality of received signals weighted by a plurality of respective weighting factors;
   converting the plurality of received signals from analog signals into digital signals and supplying the converted received signals to the digital signal processing circuit, and
   changing the plurality of weighting factors such that ratios between the plurality of weighting factors change,
   wherein the plurality of received signals includes a first received signal and a second received signal, and each of the received signals has a first signal portion corresponding to a first depth and a signal portion corresponding to a second depth, the first signal portion of each of the received signals being reflected from a portion of an object situated at the first depth into the object, the second signal portion of each of the received signals being reflected from a portion of the object situated at the second depth into the object, the first received signal being weighted by a first weighting factor, the second received signal being weighted by a second weighting factor, a ratio of the first weighting factor to the second weighting factor for the first signal portion being different from a ratio of the first weighting factor to the second weighting factor for the second signal portion, and
   wherein upon an occurrence that the digital signal processing circuit sets at least one of the plurality of weighting factors to zero, power is stopped from being supplied to at least one of a plurality of analog to digital (AD) converters, which corresponds to a received signal assigned to the at least one weighting factor set to zero.

* * * * *